United States Patent
Gustavsson

(10) Patent No.: US 7,683,178 B2
(45) Date of Patent: *Mar. 23, 2010

(54) METHOD FOR THE SYNTHESIS OF A BENZIMIDAZOLE COMPOUND

(75) Inventor: Anders Gustavsson, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 237 days.

This patent is subject to a terminal disclaimer.

(21) Appl. No.: 11/749,282

(22) Filed: May 16, 2007

(65) Prior Publication Data

US 2008/0004447 A1    Jan. 3, 2008

Related U.S. Application Data

(63) Continuation of application No. 10/531,412, filed as application No. PCT/SE03/01602 on Oct. 15, 2003, now Pat. No. 7,227,024.

(30) Foreign Application Priority Data

Oct. 18, 2002    (SE)    .................................... 0203092

(51) Int. Cl.
    *C07D 401/12*    (2006.01)
(52) U.S. Cl. .................................. 546/273.7
(58) Field of Classification Search ............... 546/273.7
    See application file for complete search history.

(56) References Cited

U.S. PATENT DOCUMENTS 4,255,431 A    3/1981    Junggren et al.
4,619,997 A    10/1986    Sih
5,391,752 A    2/1995    Hoerrner et al.
5,958,955 A    9/1999    Gustavsson et al.
6,268,502 B1    7/2001    Milac et al.
6,303,788 B1    10/2001    Cotton et al.
7,227,024 B2 *    6/2007    Gustavsson .............. 546/273.7
2006/0084811 A1    4/2006    Gustavsson

FOREIGN PATENT DOCUMENTS

WO    WO 91/18895    12/1991
WO    WO 97/22603    6/1997

OTHER PUBLICATIONS

Kuhler et al., "Structure-Activity Relationship of, etc.," J.Med.Chem. 1998, 41, 1777-1788.
The Merck Index, 13th Ed. (2001), Merck & Co., Whitehouse Station, NJ, pp. 305, 306, 369, 370, 1075, 1082, 1700, and 1718.
Purification of Laboratory Chemicals, 5th Ed. (2003), Elsevier Science (USA) Inc., New York, pp. 157, 163, and 370.

* cited by examiner

*Primary Examiner*—Patricia L Morris
(74) *Attorney, Agent, or Firm*—White & Case LLP

(57) ABSTRACT

A process for the manufacture of omeprazole or esomeprazole from pyrmethyl alcohol via pyrmethyl chloride and pyrmetazole characterized in that the whole reaction sequence is carried out without any isolation or purification of intermediates. Further, the reaction is carried out in a solvent system common for the whole reaction sequence and inert to the reactants formed during the process and used in the process and comprises a water immiscible organic solvent and a specified amount of water.

17 Claims, No Drawings

METHOD FOR THE SYNTHESIS OF A BENZIMIDAZOLE COMPOUND

This application is a continuation of U.S. patent application Ser. No. 10/531,412, filed 14 Apr. 2005, now U.S. Pat. No. 7,227,024, which is a §371 of PCT/SE2003/001602, filed 15 Oct. 2003.

The present invention relates to an improved process for the synthesis of 5-methoxy-2(((4-methoxy-3,5-dimethyl-2-pyridinyl)methyl)thio)-1H-benzimidazole (pyrmetazole) used in the manufacturing of 5-methoxy-2-[[(4-methoxy-3,5-dimethyl-2-pyridinyl)-methyl]sulphinyl]-1H-benzimidazole and its (S)-enantiomer, known under the generic names omeprazole and esomeprazole, respectively.

BACKGROUND OF THE INVENTION AND PRIOR ART

An efficient process for synthesis of omeprazole is described in WO 97/22603, which is hereby incorporated by reference. In the described process, there is no need for additional purification or isolation steps in between the different reaction steps and a more efficient process is hence offered. Further adding to the simplicity, the reaction sequence is carried is out in one common solvent system throughout the whole process. However, there is still a need of a new, even more convenient and more efficient process for the manufacturing of pyrmetazole in higher yield and with higher purity, and which process provides increased yield of the final products, omeprazole or esomeprazole.

SUMMARY OF THE INVENTION

The object of the invention is to provide a process for the manufacturing of pyrmetazole in a high yield and with a high purity, which is especially important for the asymmetric synthesis of esomeprazole. The process, i.e. the reaction sequence from pyrmethyl alcohol (Ia) to pyrmetazole (I), is carried out, without any isolation or purification of intermediates, in one solvent system common for the reaction sequence, to obtain a reproducible high yield of the final products, omeprazole or esomeprazole. Such a process eliminates time consuming steps for isolation or purification of intermediates and save time on avoiding solvent changes in the process, thus making the process more efficient and with a high production capacity.

DETAILED DESCRIPTION OF THE INVENTION

The process comprising the following reaction steps:

Step 1: Pyrmethyl alcohol (Ia)+chloro-dehydroxylating agent→pyrmethyl chloride (Ib)

Step 2: Pyrmethyl chloride (Ib)+metmercazole (Ic)→pyrmetazole (I) is performed in a solvent system common for the reaction sequence, comprising a water immiscible organic solvent and a specified amount of water added. This process is used for the synthesis of pyrmetazole, an intermediate in the synthesis of omeprazole or esomeprazole.

In Step 1, the conversion of pyrmethyl alcohol into pyrmethyl chloride, hereinafter referred to as chloro-dehydroxylation, the pyrmethyl alcohol (Ia) is reacted with an excess of a chloro-dehydroxylating agent giving an alkyl chloride, i.e. pyrmethyl chloride (Ib). The chloro-hydroxylating agent can be selected from thionyl chloride, cyanuric chloride, phosphorous trichloride, phosphorous pentachloride, and phosphorous oxychloride. The reaction is performed at a temperature of −5° C. to +45° C., preferably between −5° C. and +35° C., most preferably between +10° C. and +35° C., or between +25° C. and +35° C. In the case, where no water is present from the beginning, the conversion of the reactants into the product, pyrmethyl chloride (Ib), will not go to completion. However, the reaction can be re-started by adding a specified amount of water and the reaction thereafter can be completed. Thus, if the reaction ceases, it is possible to re-start it with addition of a specified amount of water.

According to Step 2 above, pyrmethyl chloride (Ib), provided from Step 1, is reacted with metmercazole (Ic) under alkaline conditions, e.g. an alkaline aqueous solution of metmercazole (Ic) is prepared and mixed with the pyrmethyl chloride (b). The reaction is preferably carried out at a temperature of +30° C. to +60° C. during a prolonged period of time. Metmercazole (Ic) is charged in approximately stoichiometric amount to the pyrmethyl chloride (Ib). The invention may also be used in combination with a phase transfer catalyst, for instance a quarternary amine, such as tetrabutyl ammonium bromide. The two phases formed are separated, the aqueous phase may be extracted with a water imiiscible organic solvent such as toluene, and the organic phase may be extracted with water.

As pyrmethyl alcohol (Ia) has a disadvantageous effect on the following reaction steps, it is important to minimise the content of the pyrmethyl alcohol (Ia) present.

The reaction sequence according to Step 1 and Step 2 described above is carried out in one solvent system. The solvent system used for the present reaction sequence comprises a water immiscible organic solvent, such as halogenated, aliphatic or aromatic hydrocarbons or esters, for example toluene, ethyl-acetate and methylene chloride, and a specified amount of water added. Preferably, toluene may be used as the water immiscible organic solvent.

The water content in the solvent system shall preferably be near or above the saturation point of the organic solvent used. By this, a higher amount of pyzmethyl alcohol (Ia) is allowed to react and form the pyrmethyl chloride (Ib). The amount of water may be added before, during or after the charging of the chloro-dehydroxylating agent, such as thionyl chloride. An optimum range of water present during Step 1 is between 0.3 and 5.5 mg water/ml of water immiscible organic solvent, preferably between 0.3 and 5.0 mg water/ml, or between 0.4 and 2.4 mg/ml, and most preferably between 1.0 and 2.4 mg/ml. If the water content is lower than the saturation point of the organic solvent used i.e. for toluene, less than 0.3 mg/ml, the reaction is slow and it has a tendency to stop before full conversion has been achieved. In average, a conversion of 25-50% is obtained when toluene, having a water content of less than 0.1 mg/ml, is used as the solvent system. Such a reaction leads to a high content of pyrmethyl alcohol (Ia) in the reaction mixture after Step 1. It is inconvenient to have a high content of pyrmethyl alcohol present in the crude product of pyrmetazole (I) after Step 2. We have found that if about 1%, or more, of pyrmethyl alcohol (Ia) is left in the reaction mixture, this component has an adverse effect on both the turnover and the enantioselectivity achieved in the asymmetric oxidation of pyrmetazole into esomeprazole.

The present invention is an improvement of the first two steps in the process described in WO 97/22603. The reaction sequence, from pyrmethyl alcohol (Ia) via pyrmethyl chloride (Ib) to pyrmetazole (I), is carried out in one common solvent system, comprising a water immiscible organic solvent and a specified amount of water, which is used throughout the reaction sequence. The new improved process for the manufacture of 5-methoxy-2(((4-mehoxy-3,5-dimethyl-2-pyridinyl)-methyl)-thio)-1H-benzimidazole (pyrmetazole) can in more detail be described by Step 1 and Step 2 below, both performed in a water immiscible organic solvent and with a specified amount of water added:

Step 1: Chloro-dehydroxylation:

Reacting (4-methoxy-3,5-dimethyl-2-pyridinyl)methyl alcohol (pyrmethyl alcohol) of the formula Ia

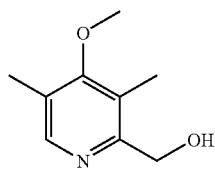

Ia with a chloro-dehydroxylating agent, such as thionyl chloride, providing (4-methoxy-3,5-dimethyl-2-pyridinyl)methyl chloride (pyrmethyl chloride) of the formula Ib

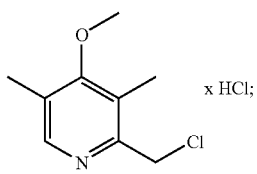

Ib

Step 2: Coupling Reaction:

Reacting (4-methoxy-3,5-dimethyl-2-pyridinyl)methyl chloride of the formula Ib, prepared in Step 1 above, with 2-mercapto-5-methoxybenzimidazole (metmercazole) of the formula Ic

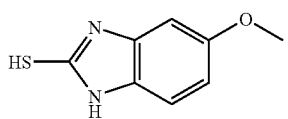

Ic in the presence of a base such as, sodium hydroxide or potassium hydroxide; providing 5-methoxy-2(((4-methoxy 3,5-dimethyl-2-pyridinyl)methyl)thio)-1H-benzimidazole (pyrmetazole) of the formula I

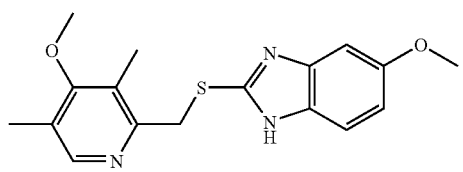

I

The pyrmetazole is then further processed to the final products, omeprazole or esomeprazole.

The present invention provides an improvement associated to Step 1 in the manufacturing of pyrmetazole, by a more complete conversion and reproducible yield of pyrmethyl alcohol (Ia) and pyrmethyl chloride (Ib) respectively. The advantageous effect of water present during the chloro-dehydroxylation reaction, Step 1, is surprisingly as this type of chloro-dehydroxylating agents are regarded as incompatible with water, i.e. thionyl chloride reacts violently with water and excess of thionyl chloride is usually hydrolysed after a reaction by an addition of water.

More specifically, the aim with the present invention has been to improve Step 1, the chloro-dehydroxylation step, in the process for preparation of pyrmetazole (I) used in the synthesis of omeprazole or esomeprazole, i.e. to obtain a more efficient conversion of the pyrmethyl alcohol (Ia), a reaction step that is common for both the synthesis of esomeprazole and omeprazole. It has, surprisingly, been shown that presence of a specified amount of water reduces the amount of remaining pyrmethyl alcohol (Ia) i.e. the conversion of pyrmethyl alcohol (Ia) according to Step 1 is more complete. A small amount of water present in the reaction mixture lead to a better conversion, and a more efficient use of pyrmethyl alcohol (Ia) and a product of high yield and high purity.

According to the process described in WO 97/22603 the crude product, pyrmetazole (I), from Step 2 is further processed to omeprazole in a consequtive reaction sequence. There is no isolation or purification performed during the reaction sequence, which is preferable with respect to process simplicity and economy. However, residues of pyrmethyl alcohol (Ia) from Step 1 have been found in the product mixture of pyrmetazole (I) in Step 2.

It has been found that traces of pyrmethyl alcohol (Ia) have disadvantageous effects upon the oxidation of pyrmetazole (I) to omeprazole and especially then in the asymmetric oxidation of pyrmetazole (I) to esomeprazole. Such traces of pyrmethyl alcohol (Ia) results in reduced turnover and enantio-selectivity in the asymmetric oxidation and give a product with less purity and in lower yield. Thus, the obtained enantiomeric excess of esomeprazole is depending on a high purity of the intermediate compound pyrmetazole (I). The impact of levels from about 1% or above of pyrmethyl alcohol has been investigated.

The presence of water in the chloro-dehydroxylation reaction, Step 1, is of outmost importance to obtain pyrmethyl chloride (Ib) and thereby pyrmetazole (I) in high yield and with a high purity without any requirements of isolation or purification. The required amount of water may be charged from the beginning, or being added during or after the addition of a suitable chloro-dehydroxylating agent, such as thionyl chloride. Preferably a small specified amount of water is charged at the beginning of the reaction. The addition of water during the process may also be used as a way to re-start an incomplete reaction to improve the yield and product purity. The present invention provides a more efficient use of the chloro-dehydroxylating agent.

Furthermore, the presence of water in Step 1 provides a safer, and more robust process, as it also reduces the different risks connected with this type of reactions, i.e. such as accumulation of thionyl chloride or reactive reaction intermediates. Thus, avoiding the risk of a late rapid exothermic reaction to occur. However, there exists other options to get complete and/or high conversion of pyrmethyl alcohol (Ia) in Step 1, and to avoid, or minimise, traces of pyrmethyl alcohol (Ia) in Step 2, These options can be, for instance, an extended reaction time, raised reaction temperature or increased excess of thionyl chloride. However, these options are not favored in view of an effective production of the final products, omeprazole and esomeprazole.

The examples that follow will further illustrate the improved process of the invention. These examples are not intended to limit the scope of the invention as defined hereinabove or as claimed below.

EXAMPLES

Example 1

Pyrmethyl alcohol, 8.82 g (52.7 mmol), was dissolved in toluene, saturated with water, 74 ml (water content 0.4 mg/ml according to Karl Fisher titration). To the stirred solution, at 10° C., thionyl chloride, 8.15 g (68.5 mmol), was added slowly over 60 minutes (flow rate 0.083 ml/min). A white precipitate was formed. The conversion of pyrmethyl alcohol into pyrmethyl chloride was followed by HPLC, (column: Nova-Pak C 18, 4 μm 3.9*150 mm). A fast reaction was recorded, reaching 99% conversion after completed addition of thionyl chloride.

Example 2

Pyrmethyl alcohol, 8.81 g (52.6 mmol), was dissolved in a mixture of toluene, 75 ml (water content 0.04 mg/ml according to Karl Fisher titration) and water, 180 μl (10 mmol, equivalent to about 2.4 mg/ml of water in toluene). To the stirred solution, at 10° C., thionyl chloride, 8.15 g (68.5 mmol), was added slowly over 60 minutes (flow rate 0.083 ml/min). A white precipitate was formed. The conversion of pyrmethyl alcohol into pyrmethyl chloride was followed by HPLC as in Example 1. A fast reaction was recorded, reaching 99% conversion after completed addition of thionyl chloride. The reaction temperature was adjusted to 20° C. and methanol, 40 ml, was added to stop the reaction. A solution of the crude product, pyrmethyl chloride was obtained, with a purity of 99.6% (HPLC), and with a pyrmethyl alcohol residue of 0.3%.

Example 3

Pyrmethyl alcohol, 8.82 g (52.7 mmol), was dissolved in toluene, 75 ml (water content 0.04 mg/ml according to Karl Fisher titration). To the stirred solution, at 10° C., thionyl chloride, 8.15 g (68.5 mmol), was added slowly over 60 minutes (flow rate 0.083 ml/min). A white precipitate was formed immediately. The obtained reaction mixture was stirred and the reaction followed by HPLC, as in Example 1, for an additional 3.5 hours (conversion declined and stopped at about 30%). Water, 180 μl (10 mmol), was added, to re-start the reaction, yielding a high conversion (>90%) within 30 minutes after the addition.

Example 4

Pyrmethyl alcohol (8.8 g, 52.6 mmol) was dissolved in toluene (75 ml, water content 0.12 mg/ml) moistened with water (180 μl, 10 mmol) at room temperature. To the stirred solution, at 25-30° C., thionyl chloride (8.15 g, 68.5 mmole) was added slowly over 60 min. (flow rate of 0.083 m/min). Conversion of the reaction was analysed with HPLC as in Example 1. Conversion over 99.5%. Water (2.3 ml) was added to quench any excess of thionyl chloride.

An alkaline (13.5 g, 168.3 mmol 50% w/w sodium hydroxide) aqueous (80 ml) solution of metmercazole (9.8 g, 54.2 mmol) was added followed by additional sodium hydroxide (8.8 g, 110.5 mmol, 50% w/w sodium hydroxide) to reach pH>12.5. The temperature was allowed to increase to 45° C. during the additions. The reaction mixture was left with vigorous stirring for approximately two hours at 45° C. The agitating was interrupted and the phases were left to separate. The aqueous phase was discarded. The organic phase, comprising pyrmetazole, was washed with water and was analysed for residues of pyrmethyl alcohol (less than 0.1% mol).

Example 5

Pyrmethyl alcohol (8.8 g, 52.6 mmol) was dissolved in toluene (75 ml, water content 0.12 mg/ml) moistened with water (375 μl, 20.8 mmol) at room temperature. To the stirred solution, at 25-35° C., thionyl chloride (9.33 g, 78.4 mmol) was added slowly over 60 min. (flow rate of 0.095 ml/min). Conversion of the reaction was analysed with HPLC as in Example 1. Conversion over 99.5%.

The synthesis continued in the same way as described in Example 4. The product phase, comprising pyrmetazole, was analysed for residue of pyrmethyl alcohol (less than 0.1% mol).

The invention claimed is:
1. A process for the manufacture of 5-methoxy-2-[[(4-methoxy-3,5-dimethyl-2-pyridinyl)-methyl]-thio]-1H-benzimidazole of formula I,

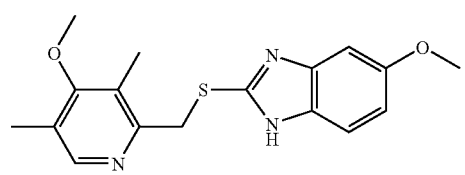

the process comprising the following reaction steps carried out in a consecutive order in a solvent system without isolation of the intermediates formed during the process:

a) reacting (4-methoxy-3,5-dimethyl-2-pyridinyl)methyl alcohol (pyrmethyl alcohol) of formula Ia,

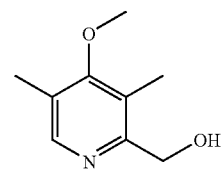

with a chloro-dehydroxylating agent to obtain (4-methoxy-3,5-dimethyl-2-pyridinyl)methyl chloride (pyrmethyl chloride) of formula Ib; and

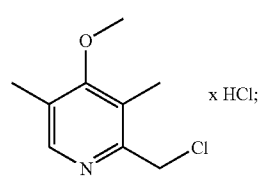

b) reacting the (4-methoxy-3,5-dimethyl-2-pyridinyl)methyl chloride of formula Ib with 2-mercapto-5-methoxy-benzimidazole (metmercazole) of formula Ic,

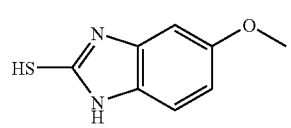

in the presence of a base to obtain 5-methoxy-2-[[(4-methoxy-3,5-dimethyl-2-pyridinyl)methyl]thio]-1H-benzimidazole (pyrmetazole) of formula I; wherein the solvent system is the same for the entire reaction sequence and comprises an organic solvent selected from the group consisting of toluene, ethyl acetate and methyl chloride and an amount of water in the range of between 0.3 and 5.5 mg water per ml of the organic solvent.

2. The process according to claim 1, wherein the organic solvent is toluene.

3. The process according to claim 1, wherein the organic solvent is ethyl acetate.

4. The process according to claim 1, wherein the water is present at the start of step a).

5. The process according to claim 1, wherein the water is added during charging of the chloro-dehydroxylating agent.

6. The process according to claim 1, wherein the water is added after charging of the chloro-dehydroxylating agent.

7. The process according to claim 1, wherein the amount of water is between the saturation point of the organic solvent and 5.5 mg/ml of the organic solvent toluene or methylene chloride.

8. The process according to claim 1, wherein the amount of water is in the range of 1.00-5.5 mg/ml of the organic solvent.

9. The process according to claim 1, wherein the amount of water is in the range of 1.0-2.4 mg/ml of the organic solvent.

10. The process according to claim 1, wherein the reaction in step a) is carried out at a temperature in the range of between −5° C. and +45° C.

11. The process according to claim 1, wherein the reaction in step a) is carried out at a temperature in the range of between −5° C. and +35° C.

12. The process according to claim 1, wherein the reaction in step a) is carried out at a temperature in the range of between +10° C. and +35° C.

13. The process according to claim 1, wherein the reaction in step a) is carried out at a temperature in the range of between +25° C. and +35° C.

14. The process according to claim 1, wherein the chloro-dehydroxylating agent is thionyl chloride.

15. The process according to claim 1, further comprising adding an additional amount of water to the organic solvent during step a) after the start of the reaction.

16. The process according to claim 1, wherein the reaction in step b) is carried out at a temperature in the range of between +30° C. and +60° C.

17. The process according to claim 7, wherein the organic solvent is toluene.

* * * * *

UNITED STATES PATENT AND TRADEMARK OFFICE
CERTIFICATE OF CORRECTION

PATENT NO. : 7,683,178 B2 Page 1 of 1
APPLICATION NO. : 11/749282
DATED : March 23, 2010
INVENTOR(S) : Anders Gustavsson It is certified that error appears in the above-identified patent and that said Letters Patent is hereby corrected as shown below:

Col. 7
Claim 1, line 6: "methyl chloride" should read
--methylene chloride--.

Signed and Sealed this

Twentieth Day of April, 2010

David J. Kappos
*Director of the United States Patent and Trademark Office*